US00PP13606P2

(12) United States Plant Patent
DeBelder

(10) Patent No.: US PP13,606 P2
(45) Date of Patent: Feb. 25, 2003

(54) HYDRANGEA PLANT NAMED 'BARBARA'

(76) Inventor: Jelena DeBelder, Hemelrijk, 93, 2910 Essen (BE)

( * ) Notice: Subject to any disclaimer, the term of this patent is extended or adjusted under 35 U.S.C. 154(b) by 0 days.

(21) Appl. No.: 10/036,938

(22) Filed: Dec. 31, 2001

(51) Int. Cl.[7] ..... A01H 5/00
(52) U.S. Cl. ..... Plt./250

(58) Field of Search ..... Plt./250

*Primary Examiner*—Bruce R. Campell
*Assistant Examiner*—June Hwu
(74) *Attorney, Agent, or Firm*—C. A. Whealy

(57) ABSTRACT

A distinct cultivar of Hydrangea plant named 'Barbara', characterized by its upright and outwardly arching plant habit; large lacy flower panicles; and panicles with large white sepals on sterile flowers with numerous small fertile flowers.

1 Drawing Sheet

BOTANICAL CLASSIFICATION/CULTIVAR DESIGNATION

*Hydrangea paniculata* cultivar Barbara.

BACKGROUND OF THE INVENTION

The present Invention relates to a new and distinct cultivar of Hydrangea plant, botanically known as *Hydrangea paniculata,* and hereinafter referred to by the cultivar name Barbara.

The new Hydrangea is a product of a breeding program conducted by the Inventor in Essen, Belgium. The objective of the breeding program was to create new Hydrangea cultivars with unique inflorescence forms.

The new Hydrangea originated from a cross-pollination by the Inventor during the summer of 1989 of two unidentified selections of *Hydrangea paniculata,* not patented. The cultivar Barbara was discovered and selected by the Inventor as a single plant within the progeny of the stated cross-pollination in a controlled environment in Essen, Belgium. Plants of the new Hydrangea differs from plants of the parent selections in plant habit, panicle form, flower size, and flower coloration.

Asexual reproduction of the new cultivar by softwood cuttings taken at Essen, Belgium, since 1995, has shown that the unique features of this new Hydrangea are stable and reproduced true to type in successive generations.

SUMMARY OF THE INVENTION

Plants of the cultivar Barbara have not been observed under all possible environmental conditions. The phenotype may vary somewhat with variations in environment such as temperature, light intensity, and daylength without, however, any variance in genotype.

The following traits have been repeatedly observed and are determined to be the unique characteristics of 'Barbara'. These characteristics in combination distinguish 'Barbara' as a new and distinct cultivar:

1. Upright and outwardly arching plant habit.

2. Large lacy flower panicles, open form.

3. Panicles with large white sepals on sterile flowers with numerous small fertile flowers.

Plants of the new Hydrangea are similar in flower color to plants of the *Hydrangea paniculata* cultivar Grandiflora, not patented. In side-by-side comparisons conducted in Grand Haven, Mich., plants of the new Hydrangea differed from plants of the cultivar Grandiflora in the following characteristics:

1. Plants of the new Hydrangea were smaller than plants of the cultivar Grandiflora.

2. Plants of the new Hydrangea were more outwardly arching and not as mounded as plants of the cultivar Grandiflora.

3. Plants of the new Hydrangea had lighter green-colored leaves than plants of the cultivar Grandiflora.

4. Plants of the new Hydrangea had more open and lacy panicles than plants of the cultivar Grandiflora.

5. Plants of the new Hydrangea had much larger, but fewer, sterile flowers than plants of the cultivar Grandiflora.

Plants of the new Hydrangea are also similar in flower color to plants of the *Hydrangea paniculata* cultivar Tardiva, not patented. In side-by-side comparisons conducted in Grand Haven, Mich., plants of the new Hydrangea differed from plants of the cultivar Tardiva in the following characteristics:

1. Plants of the new Hydrangea were smaller than plants of the cultivar Tardiva.

2. Plants of the new Hydrangea were more outwardly arching and not as upright as plants of the cultivar Tardiva.

3. Plants of the new Hydrangea had lighter green-colored leaves than plants of the cultivar Tardiva.

4. Plants of the new Hydrangea had much larger sterile flowers than plants of the cultivar Tardiva.

5. Plants of the new Hydrangea flowered earlier than plants of the cultivar Tardiva.

BRIEF DESCRIPTION OF THE PHOTOGRAPHS

The accompanying colored photographs illustrate the unique appearance of the new cultivar, showing the colors as true as it is reasonably possible to obtain in colored reproductions of this type. Colors in the photographs may differ from the color values cited in the detailed botanical description which accurately describe the colors of the new Hydrangea.

The photograph at the top of the sheet comprises a side perspective view of a typical flowering plant of 'Barbara' grown in the landscape.

The photograph at the bottom of the sheet comprises a close-up view of a typical inflorescence of 'Barbara'.

DETAILED BOTANICAL DESCRIPTION

In the following description, color references are made to The Royal Horticultural Society Colour Chart, 1995 Edition, except where general terms of ordinary dictionary significance are used. Plants used in the aforementioned photographs and in the following description were grown in Grand Haven, Mich., in an outdoor nursery and under conditions which closely approximate commercial production conditions. Plants were about 3.5 years old. The photographs and description were taken during July and August.

Botanical classification: *Hydrangea paniculata* cultivar Barbara.

Parentage:

*Male, or pollen, parent.*—Unidentified *Hydrangea paniculata* selection, not patented.

*Female, or seed, parent.*—Unidentified *Hydrangea paniculata* selection, not patented.

Propagation:

*Type cutting.*—By softwood cuttings.

*Time to initiate roots.*—About 12 days at 25° C.

*Time to produce a rooted cutting or liner.*—About 90 days at 25° C.

*Root description.*—Freely branching, and fibrous.

Plant description:

*Form/growth habit.*—Upright and outwardly arching plant habit; bushy perennial shrub. Moderately vigorous.

*Usage.*—Appropriate for one to three-gallon containers.

*Crop time.*—From rooted liners, about 10 months are required to produce a flowering finished plant in a one-gallon container.

*Plant height, soil level to top of plant plane.*—About 75 cm.

*Plant diameter or area of spread.*—About 75 cm.

*Branching habit.*—When pinched, freely branching with potentially about 77 lateral branches per plant.

*Lateral branches.*—Length: About 47 cm. Diameter: About 4 to 5 mm. Internode length: About 6 to 7 cm. Texture: Glabrous. Color: 177A.

*Foliage description.*—Leaves simple, opposite, generally symmetrical and long persisting. Deciduous. Quantity per lateral branch: Typically about 19. Length: About 12 cm. Width: About 5 cm. Shape: Elliptic to oblanceolate. Apex: Acute. Base: Acute. Margin: Serrulate. Texture, upper and lower surfaces: Slightly rugose; pubescent. Venation pattern: Pinnate. Color: Young foliage, upper and lower surfaces: 144A. Mature foliage, upper surface: 143A. Mature foliage, lower surface: 143B. Venation, upper surface: 144A. Venation, lower surface: 144B. Petiole: Length: About 3 cm. Diameter: About 2 mm. Color: 145A.

Flower description:

*Flower type and habit.*—Single sterile and fertile flowers arranged on terminal panicles; panicles large and lacy in appearance, open form. Sterile flowers with large showy sepals; without petals and reproductive organs. Fertile flowers, inconspicuous; with petals, sepals and reproductive organs. Sterile flowers persistent; fertile flowers not persistent. Sterile and fertile flowers are not fragrant.

*Natural flowering season.*—Continuously flowering from early July to late August in Grand Haven, Mich.

*Flower longevity.*—Sterile flowers last about 80 days on the plant; fertile flowers last about 1 to 2 weeks on the plant. As cut flowering stems, panicles last about 3 weeks.

*Quantity of flowers.*—Freely flowering; one terminal panicle per lateral branch with about 38 sterile flowers and about 934 fertile flowers per panicle.

*Panicle height.*—About 20 cm.

*Panicle diameter.*—About 12 cm.

*Panicle shape.*—Conical, broad at base.

*Flower diameter.*—Sterile flowers: About 8 cm. Fertile flowers: About 9 mm.

*Flower depth (height).*—Sterile flowers: About 1 cm. Fertile flowers: About 8 mm.

*Flower buds (sterile and fertile flowers).*—Length: About 5 mm. Diameter: About 6 mm. Shape: Obovate. Color: Initially 149D, then when opening, 155A.

*Petals (petals present only on fertile flowers; sterile flowers do not have petals).*—Arrangement: About five. Length: About 5 mm. Width: About 2 mm. Shape: Lanceolate. Apex: Acute. Base: Attenuate. Margin: Entire. Texture, upper and lower surfaces: Smooth, glabrous. Color: When opening, upper and lower surfaces: 155A. Fully opened, upper and lower surfaces: 155C; color more towards 155A with subsequent development.

*Sepals.*—Quantity per flower: Fertile flowers: About five, fused into a calyx. Sterile flowers: About four or five. Length: Fertile flowers: About 4 mm. Sterile flowers: About 5.5 cm. Width: Fertile flowers: About 3 mm. Sterile flowers: About 2.5 cm. Shape: Fertile flowers: Ovate and lanceolate. Sterile flowers: Oblanceolate to obovate. Apex: Fertile flowers: Acute. Sterile flowers: Obtuse to retuse. Base: Fertile flowers: Fused. Sterile flowers: Attenuate. Margin: Fertile flowers: Entire. Sterile flowers: Entire to occasionally serrulate. Texture, fertile and sterile flowers, upper and lower surfaces: Smooth, glabrous. Color: Fertile flowers: When opening and fully opened, upper and lower surfaces, 155A. Sterile flowers: When opening, upper and lower surfaces: 155A. Fully opened, upper and lower surfaces: 155C; color more towards 155A with subsequent development.

*Pedicels.*—Angle: Sterile flowers: About 160° from vertical. Fertile flowers: About 90 to 160° from vertical. Strength, sterile and fertile flowers: Strong. Length: Sterile flowers: About 3.5 cm. Fertile flowers: About 4 mm. Diameter: Sterile flowers: About 2.5 mm. Fertile flowers: About 2 mm. Color, sterile and fertile flowers: 155A.

*Peduncles.*—Angle: Erect. Strength: Strong. Length: About 16.5 cm. Diameter: About 2 to 4 mm. Color: Close to 145A.

*Reproductive organs (reproductive organs present only on fertile flowers; sterile flowers do not have reproductive organs)*—Stamens: Quantity per flower: About 10 to 13. Anther shape: Round. Anther length: About 1 mm. Anther color: 162D. Pollen amount: Scarce Pollen color: 155B. Pistils: Pistil quantity per flower: Three, fused. Pistil length: About 1.5 mm.

Stigma shape: Three-lobed. Stigma color: 4D. Style length: About 0.5 mm. Style color: 4D.

*Fruit*.—Type: Capsule, dehiscent. Length: About 5 mm. Diameter: About 3 mm. Shape: Urn-shaped. Color: Close to 177A.

*Seed*.—Minute, dust-like. Length: About 2 mm. Diameter: Less than 0.5 mm. Color: Close to 177A.

Disease/pest resistance: Under commercial production conditions, plants of the new Hydrangea have not been observed to be resistant to pathogens or pests common to Hydrangea.

Weather tolerance: Plants of the new Hydrangea have been shown to be tolerant to temperatures ranging from −30 to 33° C. Flowers of plants of the relatively tolerant to wind and rain.

It is claimed:

1. A new and distinct cultivar of Hydrangea plant named 'Barbara', as illustrated and described.

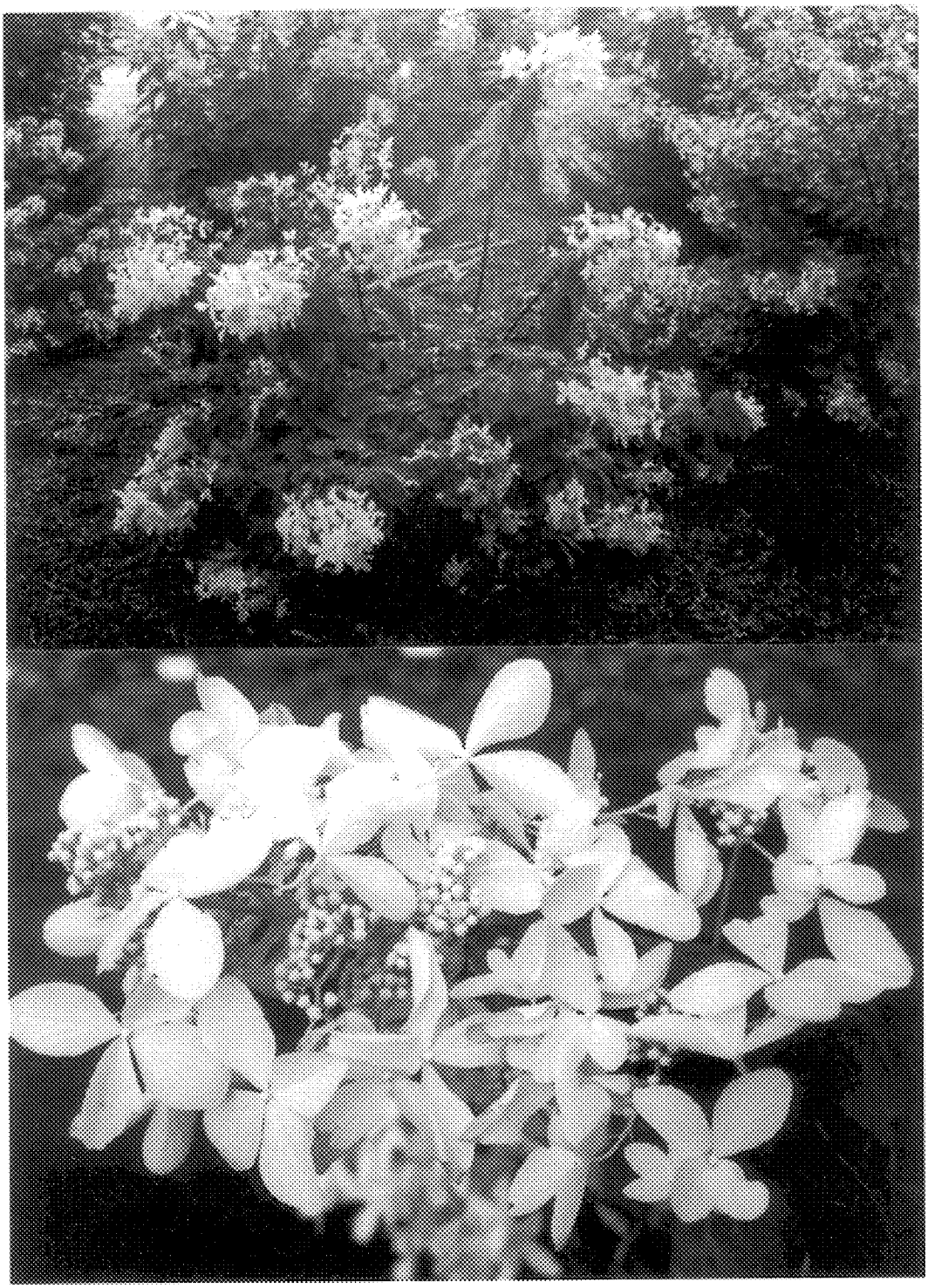

* * * * *